United States Patent [19]

Bertus et al.

[11] 4,334,979
[45] Jun. 15, 1982

[54] HYDROCARBON CRACKING PROCESS USING A CATALYST CONTAINING GERMANIUM

[75] Inventors: Brent J. Bertus; Dwight L. McKay, both of Bartlesville, Okla.

[73] Assignee: Phillips Petroleum Company, Bartlesville, Okla.

[21] Appl. No.: 139,483

[22] Filed: Apr. 11, 1980

[51] Int. Cl.$^3$ ............................................. C10G 11/05
[52] U.S. Cl. ............................. 208/114; 208/52 CT; 208/120; 252/411 R; 252/437; 252/439; 252/455 Z
[58] Field of Search ................................ 208/114, 120

[56] References Cited

U.S. PATENT DOCUMENTS

| | | | |
|---|---|---|---|
| 2,129,693 | 8/1935 | Houdry | 208/119 |
| 2,564,268 | 8/1951 | Mathy et al. | 208/114 |
| 2,901,419 | 8/1959 | Brill | 208/119 |
| 2,921,018 | 1/1960 | Helmers et al. | 208/114 |
| 3,297,565 | 1/1963 | Garwood et al. | 208/217 |
| 3,423,316 | 1/1969 | Dickert et al. | 252/32.7 |
| 3,832,449 | 8/1974 | Rubin et al. | 208/120 X |
| 3,977,962 | 8/1976 | Arey et al. | 208/59 |
| 4,031,002 | 6/1977 | McKay | 208/113 |

OTHER PUBLICATIONS

Technical Service Comments, Davison Chemical Div. of W. R. Grace and Co., pp. 3, 8, 9, 27, 28.

*Primary Examiner*—Delbert E. Gantz
*Assistant Examiner*—G. E. Schmitkons

[57] ABSTRACT

A hydrocarbon is catalytically cracked employing a cracking catalyst contacted with a treating agent selected from germanium and germanium compounds.

22 Claims, No Drawings

HYDROCARBON CRACKING PROCESS USING A CATALYST CONTAINING GERMANIUM

BACKGROUND OF THE INVENTION

This invention relates to a process for cracking a hydrocarbon feedstock. In another aspect, the invention relates to a process for passivating contaminants on a cracking catalyst. In still another aspect, the invention relates to a cracking catalyst.

Contaminants, for example, nickel, vanadium and iron are found in significant concentrations in heavy oil fractions and lower quality crude oil. These contaminants have a poisoning effect on the expensive cracking catalysts employed to convert crude oil into gasoline and other valuable petroleum products, frequently making exploitation of these oils economically unattractive. Unfortunately, because of limited supplies of oils containing low levels of contaminants, it is sometimes necessary to employ the metals-contaminated oils in catalytic cracking processes.

The contaminants found in feedstocks to cracking processes become deposited on the cracking catalyst. The deposition on the catalyst of, for example, nickel, vanadium and iron, causes a decrease in the activity of the cracking catalyst to convert the hydrocarbon feedstock into cracked products, including gasoline. The selectivity of the cracking catalyst for cracking the feedstock into gasoline, as manifested by the portion of cracked products comprising gasoline, is also decreased. The production of undesirable products, for example, hydrogen and methane, which must be compressed, necessitating additional equipment; and coke, which is deposited on the catalyst and must be burned off, requiring additional equipment and "off-time" during which the catalyst is not employed for cracking, is significantly increased.

Because of these problems, the industry usually replaces cracking catalysts contaminated by more than about 3,000 parts per million (ppm) of vanadium equivalents of vanadium and nickel, defined as the sum of the parts by weight of vanadium and four times the parts by weight of nickel in one million parts by weight of contaminated cracking catalyst. This level of contamination is rapidly reached when cracking heavily contaminated feedstocks. There is thus a need for a cracking process suitable for use with contaminated feedstocks and contaminated cracking catalysts. This is also a need for a cracking catalyst which is only minimally adversely affected by deposits thereon of contaminants selected from nickel, vanadium and iron. There is also a need for a process of treating a contaminated cracking catalyst to increase its activity for conversion and selectivity for producing gasoline and to decrease its selectivity for producing undesirable products, for example, hydrogen and coke.

OBJECTS OF THE INVENTION

It is thus an object of the present invention to provide an improved catalytic cracking process well adapted for cracking metals containing feedstocks.

Another object of this invention is to provide a process for the passivation of contaminants deposited on a cracking catalyst and thus reduce their adverse effects on the cracking process.

Another object of the invention is to provide a process for at least partially restoring used cracking catalyst so that it can continue to be economically employed in a catalytic cracking process.

Another object of this invention is to provide a modified cracking catalyst which has a low susceptibility to metals poisoning.

Another object of this invention is to provide a cracking catalyst which provides high yields and selectivity for gasoline or higher-boiling hydrocarbon fuel and remains highly selective as contaminants become deposited thereon.

Other aspects, objects and the several advantages of the invention will be readily apparent to one skilled in the art from the following disclosure and the appended claims.

SUMMARY OF THE INVENTION

In accordance with the invention, a cracking catalyst composition comprises a cracking catalyst in combination with a treating agent selected from germanium and germanium compounds.

Further, according to the invention, a hydrocarbon feedstock is catalytically cracked employing the above-described catalyst composition.

Still further, according to the invention, at least one metal selected from nickel, vanadium and iron in contact with a cracking catalyst is passivated by contacting the cracking catalyst with a treating agent selected from germanium and germanium compounds.

Still further, according to the invention, a used cracking catalyst containing at least 3,000 ppm vanadium equivalents is at least partially restored upon contact with a treating agent selected from germanium and germanium compounds.

DETAILED DESCRIPTION OF THE INVENTION

It has been discovered that the adverse effects of metals, for example, the adverse effects caused by nickel, vanadium and iron on a cracking catalyst can be precluded or reduced by contacting the cracking catalyst with a treating agent selected from germanium and germanium compounds. The treating agent can be selected from elemental germanium, inorganic germanium compounds, organic germanium compounds, and mixtures or solutions having at least one germanium treating agent. Most any germanium-containing composition is believed to be suitable. Examples of inorganic germanium compounds which can be employed include the halides, nitrides, hydrides, oxides, sulfides, selenides, tellurides, imides, sulfates, and phosphates of germanium in any of its valence states and mixtures of any two or more of such compounds. Germanium containing materials, for example, argyrodite and canfieldite, and germanium containing impure materials, for example, those recovered during the process of other metals, such as, zinc germanate and magnesium germanate are also believed to be suitable sources of germanium. Examples of organic germanium compounds which can be employed include germanium compounds of the formula

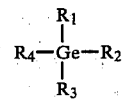

wherein $R_1$, $R_2$, $R_3$ and $R_4$ are independently selected from the group consisting of hydrogen, halogen, hydrocarbyl and oxyhydrocarbyl. The above formula is intended to include germanium compounds wherein two $R_x$ groups represent the same radical, as in germanium complexes, for example, germanium citrate. The hydrocarbyl and oxyhydrocarbyl radicals can have, for example, from 1–20 carbon atoms and can be substituted, for example, with halogen, nitrogen, phosphorus or sulfur. Exemplary hydrocarbyl and oxyhydrocarbyl radicals are alkyl, alkenyl, cycloalkyl, aryl, and combinations thereof, for example, alkylaryl or alkylcycloalkyl. Thus, germanium compounds such as tetrabutylgermanium, germanium tetrabutoxide, tetraphenyl germanium, germanium tetraphenoxide, germanium tetrakis(thiophenoxide), triphenylgermanium thiobenzoate, or diphenyldibromogermanium can be employed in the present invention.

The presently preferred treating agents are the germanium salts of hydrocarbyl-phosphoric and hydrocarbyl-thiophosphoric acids. The compositions are conveniently represented by the formula

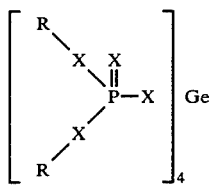

wherein R is hydrocarbyl having 1–20 carbon atoms and X is independently selected from oxygen and sulfur. Preferably, R is alkyl having from 1 to about 6 carbon atoms because of commercial availability of suitable synthesis materials, the oil solubilities of the represented composition wherein R has 1–6 carbon atoms, and because compositions having between 1 and about 6 carbon atoms in the R group have been tested with good results. These compositions can be formed, for example, by the double decomposition reaction between a germanium tetrahalide, for example, germanium tetrachloride, and a potassium salt of a selected hydrocarbyl-phosphoric or hydrocarbyl-thiophosphoric acid, for example, potassium di-n-propylphosphorodithioate. The desired germanium salt can be separated from the potassium chloride by-product by methods known in the art. The organic moieties can be alkyl, aryl, cycloalkyl, alkylaryl, arylakyl, alkenyl, alkenyl-aryl and the like in nature. Compositions represented by the formula

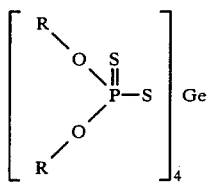

wherein R is as defined before are preferred because of ease of synthesis. Germanium tetrakis(di-n-propylphosphorodithioate) is the treating agent presently preferred, because it has been employed with good results.

Mixtures or solutions having one or more germanium treating agents are also operable. In addition to at least one germanium treating agent, mixtures or solutions employed can also desirably contain elements or compositions containing elements selected from groups IVA, VA and VIA of the periodic table as published in the *Handbook of Chemistry and Physics*, Chemical Rubber Company, 45th ed., 1964, p. B-2. Thus, compounds, solutions and mixtures which contain elements selected from the group consisting of tin, phosphorous, antimony, bismuth, sulfur, selenium and tellurium can be employed in addition to germanium treating agents to at least partially preclude or mitigate the undesirable effects of metals on the cracking catalyst. Sulfides, selenides and tellurides of tin, antimony and bismuth and sulfates, phosphates and thiophosphates of tin, antimony and bismuth as well as hydrocarbyl and oxyhydrocarbyl derivatives of these elements and compounds are exemplary of non-germanium compounds which can be advantageously employed in conjunction with the selected germanium treating agent. The presently preferred treating agent of this class is a mixture of germanium tetrakis(di-n-propylphosphorodithioate) and antimony tris(di-n-propylphosphorodithioate) because it has been employed with good results and is oil-soluble. The preferred mixture has a weight ratio of germanium to antimony of between about 1:100 to about 100:1, more preferably between about 1:10 to about 1:1, because a mixture within this range has been employed with good results.

Because the main purpose of germanium on the cracking catalyst material is to prevent or mitigate the otherwise (without germanium) occurring undesirable effects of contaminating metals, in particular the increased hydrogen and coke production and the reduced yield of gasoline or higher-boiling hydrocarbon fuels such as kerosene, diesel fuel and burning oils caused by these contaminating metals, the sources of germanium utilized and incorporated into or onto the cracking catalyst should be essentially free of contaminating metals. Accordingly, it is desirable that the germanium sources should essentially contain no nickel, no vanadium and no iron.

The treating agent can be contacted with used cracking catalyst, unused cracking catalyst, or a mixture thereof in accordance with the present invention and prior to, and/or during the use of the catalyst. Use of the treating agent with used cracking catalyst increases catalyst activity, increases catalyst selectivity for gasoline production, and surprisingly, decreases the production of hydrogen and the production of coke. Likewise, use of the treating agent with new cracking catalyst maintains high activity and selectivity and low hydrogen and coke production. The term "cracking catalyst" as used herein refers to either new or used zeolite-containing cracking catalyst materials which are useful for cracking hydrocarbons in the absence of added hydrogen.

The cracking catalyst advantageously treated in accordance with the present invention can be any zeolite-containing cracking catalyst suitable for catalytic cracking of hydrocarbons which is susceptible to becoming deleteriously affected by the presence of one or more of the metals of nickel, vanadium and iron. Such catalysts are often used to catalytically crack hydrocarbons boiling above 400° F. (204° C.) for the production of gasoline, motor fuel blending components and light distillates. Some of the more common cracking catalysts generally contain silica or silica-alumina, such materials being associated with the zeolitic component. These zeolitic materials can be naturally occurring, or they can be manufactured by methods well known in the art. The zeolite materials are often ion exchanged with metallic ions and/or ammonium ions to improve the activity and/or selectivity of the catalyst. Zeolite-modified silica-alumina catalysts are particularly applicable in this invention, especially those silica-alumina catalysts comprised of from about 1 to about 60% zeolitic material. Examples of cracking catalysts useful in the present invention include, for example, hydrocarbon cracking catalysts obtained by admixing an inorganic oxide gel with an aluminosilicate and aluminosilicate compositions which are strongly acidic as a result of treatment with a fluid medium containing at least one rare earth metal cation and a hydrogen ion, or ion capable of conversion to a hydrogen ion. The catalytic cracking materials can vary widely in pore volume and surface area. Generally, however, the unused cracking catalyst will have a pore volume in the range of about 0.1 to about 1 mL/g. The surface area of this unused catalytic cracking material generally will be in the range of about 50 to about 500 m$^2$/g. Preferably, the cracking catalyst is suitable for use in a fluid catalytic cracking process. In a fluid catalytic cracking process, the unused catalytic cracking material employed will generally be in particulate form having a particle size principally within the range of about 10 to about 200 microns. The preferred cracking catalysts are commonly referred to as FCC catalysts, and are well known by those skilled in the art.

The unused catalytic cracking material will often exhibit concentrations of nickel vanadium, and iron within the following ranges, although for best results it is preferred that the unused catalytic cracking material contain essentially no nickel or vanadium:

| | |
|---|---|
| nickel | 0 to 0.02 weight percent |
| vanadium | 0 to 0.06 weight percent |
| iron | 0 to 0.8 weight percent. |

The weight percentages in this table relate to the total weight of the unused catalytic cracking material including the metals nickel, vanadium and iron, but excluding the added germanium treating agent. The contents of these metals on the cracking catalyst can be determined by standard methods well known in the art, e.g., by atomic absorption spectroscopy or by X-ray fluorescence spectroscopy.

During use, the cracking catalysts become slowly deactivated from accumulations thereon of contaminants from the hydrocarbon feedstock. The accumulated contaminants also adversely affect the selectivity of the cracking catalyst for cracking the feedstock to desirable products. The cracking catalyst produces more hydrogen and coke, and less gasoline, from the hydrocarbon feedstock. The contaminants which accumulate on the cracking catalyst include nickel, vanadium and iron, although a large portion of the iron detected during analysis of used cracking catalyst is so-called "tramp iron", and has as its origin eroded ferrous equipment, rather than the hydrocarbon feedstock. Tramp iron is believed to have little effect on the cracking ability of the catalyst. Because it is difficult to distinguish tramp iron on the catalyst from catalytically active iron, the degree to which the catalyst is contaminated is often assessed in terms of vanadium equivalents of contaminating metals, which is a measure of the accumulations of only vanadium and nickel. The vanadium equivalents of contaminants on the cracking catalyst is expressed herein in parts per million (ppm) and is the sum of the parts by weight of vanadium and four times parts by weight of the nickel on one million parts by weight of contaminated cracking catalyst.

The activity and selectivity of untreated cracking catalyst declines as metals become deposited on the catalyst from the feedstock. Usually the activity and selectivity of the cracking catalyst have so declined by the deposit thereon of about 3000 vanadium equivalents that it is uneconomical to continue its employment for cracking. However, the observable improvement in the activity and selectivity of the cracking catalyst upon treatment with the germanium containing treating agent in accordance with the present invention increases with increasing levels of contaminants on the cracking catalyst. Thus, in accordance with the present invention, catalysts having deposited thereon in excess of 3,000 ppm of vanadium equivalents generally can be regenerated to the point where they can be economically employed in a cracking process, for example, the cracking of heavy oils. In one aspect of the present invention, it is preferable that the cracking catalyst to be treated be a used catalyst having deposited thereon at least 3,000 ppm vanadium equivalents thereby reacting a deactivated cracking catalyst that might otherwise have to be disposed of. When employed in this manner, treatment of the cracking catalyst in accordance with the invention is effective to at least partially reactivate deactivated cracking catalysts containing 6,000, 10,000 and even 20,000 and beyond vanadium equivalents.

The amount of treating agent contacted with the cracking catalyst can be selected over a wide range. Generally, the amount of treating agent employed will be sufficient to impart to the cracking catalyst a "passivating amount" of germanium. By "passivating amount" is meant an amount of treating agent effective to mitigate an adverse effect caused by the presence of nickel, vanadium or iron in contact with the cracking catalyst. A passivating amount of germanium treating agent is dependent, at least to some extent, on the amounts and activities of the contaminants deposited or expected to be deposited on the cracking catalyst. The activity of a particular contaminant to detrimentally affect the cracking process is generally dependent on factors such as its residence time on the catalyst and its identity. In addition, certain combinations of contaminants may cooperate synergistically to cause adverse effects. The amount of germanium treating agent necessary to passivate a given amount of metals on an equilibrium cracking catalyst can be approximated in terms of the vanadium equivalents of contaminating metals deposited on the catalyst for many fluid catalytic cracking operations. Expressed in these terms, a passivating amount of germanium treating agent, expressed as the ratio between the elemental weight of germanium to vanadium equivalents on the cracking catalyst, is generally in the range of from about 1:5000 to about 5:1, more preferably from about 1:1000 to about 1:1, and most preferably from about 1:500 to about 1:5. The broad range is believed to be the general range in which the present invention would be employed for most equilibrium catalysts, the intermediate range is believed to be the range in which the invention would be more often employed and the narrowest range is provided as a range which has provided good results.

The amount of germanium on the treated cracking catalyst will generally be from 0.0001 to about 4 parts by weight germanium per 100 parts by weight of treated cracking catalyst, i.e., the weight of cracking catalyst with the treating agent and contaminants deposited thereon. For cracking catalysts in which germanium atoms have been substituted for the conventionally employed silicon atoms, all weight ranges used herein refer to the weight of germanium added to the catalyst as the treating agent. Usually, it is believed that a weight range of germanium of from about 0.001 to about 1 part by weight germanium per 100 parts by weight of treated cracking catalyst will provide very good results. It appears most desirable to maintain a germanium concentration on the catalyst of between about 0.01 to about 0.5 parts by weight of germanium per 100 parts by weight of treated cracking catalyst, because compositions having germanium concentrations within this range have been tested with excellent results.

The manner in which the treating agent is contacted with the cracking catalyst is not critical. The treating agent can be contacted with the cracking catalyst in any manner effective to impart to the cracking catalyst a passivating concentration of germanium. For example, the agent in finely divided form can be mixed with a cracking catalyst in ordinary manner such as by rolling, shaking, stirring or the like. Alternatively, the treating agent can be dissolved or dispersed in a suitable liquid, e.g., water, hydrocarbon or aqueous acid, depending in part on the particular treating agent used, and the resulting solution or dispersion can be used to impregnate the cracking catalyst, followed by volatilization of the liquid, or the treating agent can be precipitated onto the catalyst from a solution of the treating agent followed by solvent removal, or, the treating agent can be sprayed onto the catalyst. Preferably, the treating agent is dissolved or dispersed in the hydrocarbon feedstock used in a fluid catalytic cracking process, in which instance the hydrocarbon feedstock and the treating agent contact the cracking catalyst at about the same time. Also, if desired, the cracking catalyst can be exposed to the treating agent in vapor form to deposit the agent on the catalyst. Of course, combinations of these various methods can be employed to produce the modified cracking catalyst of the present invention.

The feedstocks employed in the catalytic cracking process of this invention can and generally do contain metal contaminants, for example, nickel, vanadium and iron. The feedstocks include those which can be utilized in catalytic cracking processes to produce gasoline and light distillate fractions from heavier hydrocarbon feedstocks. The feedstocks generally have an initial boiling point above about 400° F. (204° C.) and include fluids such as gas oils, fuel oils, heavy oils, cycle oils, slurry oils, topped crudes, shale oils, oils from tar sands, oils from coal, mixtures of two or more of these, and the like. By "topped crude" is meant those oils which are obtained as the bottoms of a crude oil fractionator. If desired, all or a portion of the feedstock can constitute an oil from which a portion of the metal content previously has been removed, e.g., by hydrotreating or solvent extraction.

A preferred embodiment of the cracking process of this invention utilizes a cyclic flow of catalyst from a cracking zone to a regeneration zone. In this process, a hydrocarbon feedstock containing contaminating metals, for example, nickel, vanadium and iron, is contacted in a cracking zone under cracking conditions and in the absence of added hydrogen with a fluidized cracking catalyst which has been treated in accordance with the invention; a cracked product is obtained and recovered; the cracking catalyst is passed from the cracking zone into a regeneration zone; and in the regeneration zone the cracking catalyst is regenerated by being contacted with a free oxygen-containing gas, preferably air. The coke that has been built up during the cracking process is thereby at least partially burned off the catalyst. The regenerated cracking catalyst is reintroduced into the cracking zone for contact with additional feedstock.

Furthermore, it is preferred in carrying out the cracking process of this invention to replace a fraction of the total cracking catalyst by unused cracking catalyst continuously or intermittently. Generally, about 0.5 to about 7 weight percent of the total cracking catalyst is replaced daily by a fresh cracking catalyst. The actual quantity of the catalyst replaced depends in part upon the nature of the feedstock used. Where the feedstock used in heavily laden with contaminants, a larger amount of cracking catalyst is replaced daily, optimally so that the amount of catalyst withdrawn daily has an amount of contaminants deposited thereon which is equal to the amount of contaminants newly deposited daily on the catalyst inventory; i.e., a sufficient amount of catalyst inventory is replaced daily to maintain the amounts of contaminants on the catalyst at an equilibrium level. The make-up quantity of cracking catalyst can be added at any location in the process. Preferably, however, the cracking catalyst that is make-up catalyst is introduced into the regeneration zone in the cyclic cracking process.

Also, it is to be understood that the used cracking catalyst coming from the cracking zone, before introduction into the regenerator, is stripped of essentially all entrained liquid or gaseous hydrocarbons. Similarly, the regenerated catalyst can be stripped of any entrained oxygen before it reenters the cracking zone. The stripping is generally done with steam.

The specific conditions in the cracking zone and in the regeneration zone are not critical and depend upon several parameters, such as the feedstock used, the catalyst used, and the results desired. Preferably and most commonly, the cracking and regeneration conditions are within the following ranges:

| Cracking Zone | |
|---|---|
| Temperature: | 800-1200° F. (427°-649° C.) |
| Cracking Time: | 1-40 seconds |
| Pressure: | Subatmospheric to 3000 psig |
| Catalyst:oil ratio | 3:1 to 30:1, by weight |
| Regeneration Zone | |
| Temperature: | 1000°-1500° F. (538°-816° C.) |
| Catalyst Regeneration Time: | 2-40 minutes |
| Pressure: | Subatmospheric to 3000 psig |
| Regeneration Air at 60° F. | 100-250 ft$^3$/lb. coke |
| (16° C.) and 1 atmosphere: | (6.2-15.6 m$^3$/kg coke) |

Advantageously, and in accordance with a preferred emb odiment of this invention, the treating agent selected from germanium and germanium compounds is added to the feedstock entering the cracking zone to form a solution or mixture which contacts the contaminated fluidized cracking catalyst in the cracking zone. Typically, this feedstock will contain one or more of the metals within the ranges shown in Table I:

TABLE I

| Metal | Metal Content of Feedstock, ppm[1] |
|---|---|
| Nickel | 0.02 to 100 |
| Vanadium | 0.02 to 500 |
| Iron | 0.02 to 500 |
| Total effective metals | 0.2 to 1400[2] |

[1] The ppm metal content refers to the feedstock as used. As used in this table and throughout the specification, ppm means parts per million, by weight.
[2] Total effective metals in this table refer to the sum of the vanadium, iron and 4 times the nickel contents in the feedstock that are effective in contaminating the catalyst; the total metals content can be determined in accordance with methods well known in the art, e.g., by atomic absorption spectroscopy.

Most preferably, the germanium-containing treating agent is metered continuously into the catalytic cracker along with the feedstock at at least a rate which is related to the amounts of contaminants in the feedstock set forth in Table II:

TABLE II

| Total Effective Metals in Feedstock (ppm)[1] | Germanium Concentration in Feedstock (ppm) |
|---|---|
| <1-40 | 0.005-20 |
| 40-100 | 0.2-50 |
| 100-200 | 0.5-100 |
| 200-300 | 1.0-200 |
| 300-800 | 2.0-500 |

[1] Fe(ppm) + V(ppm) + 4 Ni(ppm)

One of the most important embodiments of this invention resides in a heavy oil cracking process. Most known commercial heavy oil cracking processes are capable of cracking heavy oils having a metals content of up to 100 ppm of total effective metals as defined above but with only economically marginal results obtained with oils having 50 to 100 ppm of total effective metals. This is because the catalyst becomes rapidly deactivated from accumulated contaminants. In accordance with this invention, heavy oils with a total metals content of about 50 to 100 ppm and even those of about 100 to 200 ppm and above of total metals can be cracked in a cracking process by utilizing the treated cracking catalyst to yield gasoline and other fuels and fuel blending components. Thus, heavy oils with total metals contents of from 100 to 300 ppm that could not be directly used for fuel production in most known processes, and in particular for gasoline or higher-boiling hydrocarbon fuels production, in accordance with this invention can be cracked to yield gasoline and higher-boiling hydrocarbon fuels such as kerosene, diesel fuel and burning oils.

The invention will be still more fully understood from the following example, which is intended to illustrate a preferred embodiment of the invention but not to limit the scope thereof.

EXAMPLE I

A commercial cracking catalyst comprising amorphous silica-alumina associated with zeolitic material, which had been used in a commercial cracking unit and subsequently subjected to regeneration in the laboratory, was employed in tests which demonstrated the advantageous use of germanium in improving a metals-contaminated used cracking catalyst. The catalyst contained in excess of 20,000 ppm vanadium equivalents of nickel and vanadium. Properties of the used cracking catalyst prior to regeneration in the laboratory are shown in Table III.

TABLE III

| Surface area, m²/g | 74.3 |
|---|---|
| Pore volume, mL/g | 0.29 |
| Composition, weight % | |
| Aluminum | 21.7 |
| Silicon | 24.6 |
| Nickel | 0.38 |
| Vanadium | 0.60 |
| Iron | 0.90 |
| Cerium | 0.40 |
| Sodium | 0.39 |
| Carbon | 0.06 |

This catalyst contained 21,200 vanadium equivalents.

The used commercial cracking catalyst having the properties shown in Table III was then subjected to regeneration in the laboratory by heating the catalyst while fluidized with air to 1200° F. (649° C.) and maintaining it at that temperature for about 30 minutes while fluidized with air. The catalyst was then cooled to room temperature (about 25° C.) while fluidized with nitrogen, and the resulting regenerated catalyst, herein designated as catalyst O, was employed as shown below.

A portion of catalyst O was used in the preparation of a catalyst composition containing 0.5 part by weight germanium per 100 parts by weight catalyst O. This was done by mixing 35 g of catalyst O with a solution of 0.92 g tetraphenylgermanium in 35 mL cyclohexane. The mixture was then dried by heating to 500° F. (260° C.) on a hot plate.

The above catalyst comprising germanium was conditioned in the following manner. The catalyst was placed in a laboratory-sized, confined fluid bed, quartz reactor and heated from room temperature (about 25° C.) to 900° F. (482° C.) while fluidized with nitrogen, then heated from 900° F. (482° C.) to 1200° F. (649° C.) while fluidized with hydrogen. While maintained at about 1200° F. (649° C.), the catalyst was then fluidized with nitrogen for 5 minutes, followed by fluidization with air for 15 minutes. The catalyst was then aged through 10 cycles, each cycle being conducted in the following manner. The catalyst was cooled from 1200° F. (649° C.) to about 900° F. (482° C.) during 0.5 minute while fluidized with air, then fluidized with nitrogen while maintained at approximately 900° F. (482° C.) for about 1 minute, then heated to 1200° F. (649° C.) during 2 minutes while fluidized with nitrogen and hydrogen, then maintained at 1200° F. (649° C.) for 1 minute while fluidized with nitrogen, and then maintained at 1200° F. (649° C.) for 10 minutes while fluidized with air. After these 10 aging cycles the catalyst was cooled to room temperature (about 25° C.) while fluidized with nitrogen to provide a catalyst herein designated as catalyst A.

Catalysts O and A were evaluated in two series of cracking-regeneration cycles, using approximately 34-35 g of catalyst as a confined fluid bed in a quartz reactor and employing topped West Texas crude oil as the feedstock in the cracking step. Properties of the topped West Texas crude oil are shown in Table IV.

TABLE IV

| API gravity @ 60° F. (16° C.)[1] | 21.4 |
|---|---|
| Distillation, °F. (°C.)[2] | |
| IBP | 556 (291) |
| 10% | 803 (428) |
| 20% | 875 (468) |
| 30% | 929 (498) |
| 40% | 982 (528) |
| 50% | 1031 (555) |

TABLE IV-continued

| | |
|---|---|
| Carbon residue, Ramsbottom, wt %[3] | 5.5 |
| Elemental analysis | |
| S, wt % | 1.2 |
| Ni, ppm | 5.24 |
| V, ppm | 5.29 |
| Fe, ppm | 29 |
| Pour point, °F. (°C.)[4] | 63 (17) |
| Kinematic viscosity, cSt[5] | |
| @ 180° F. (82° C.) | 56.5 |
| @ 210° F. (99° C.) | 32.1 |
| Refractive index @ 67° C.[6] | 1.5 |

[1]ASTM D 287-67
[2]ASTM D 1160-61
[3]ASTM D 524-64
[4]ASTM D 97-66
[5]ASTM D 445-65
[6]ASTM D 1747-62

In each cracking-regeneration cycle the cracking step was carried out at 950° F. (510° C.) and about atmospheric pressure for 0.5 minute, and the regeneration step was conducted at about 1200° F. (649° C.) and about atmospheric pressure for approximately 0.5 hour using fluidizing air, the reactor being purged with nitrogen before and after each cracking step. Catalyst A was evaluated at catalyst:oil weight ratios of 7.32 and 7.55. Catalyst O was evaluated under various conditions, including varying catalyst:oil weight ratios. Among the many tests carried out, the three tests with catalyst O most comparable to those conducted with catalyst A were carried out at catalyst:oil weight ratios of 6.81, 7.70 and 7.67, ratios which straddle those used in the evaluation of catalyst A. Except for the variation in catalyst:oil weight ratios as noted, these five tests of the two catalysts with or without the use of a germanium treating agent were conducted under comparable conditions. Results of these five evaluations are summarized in Table V.

TABLE V

| Run No. | Catalyst | Catalyst[2]:Oil[3] Weight Ratio | Conversion, Vol % of Feed | Yield Coke, Wt % of Feed | Yield H$_2$, SCF/bbl Feed Converted | Yield Gasoline[4], Vol % of Feed | Selectivity to Gasoline[1], Vol % |
|---|---|---|---|---|---|---|---|
| 1 | O | 6.81 | 72.5 | 17.0 | 789 | 51.5 | 71.0 |
| 2 | O | 7.70 | 74.9 | 17.7 | 896 | 54.7 | 73.0 |
| 3 | O | 7.67 | 74.7 | 15.6 | 828 | 52.2 | 69.8 |
| 4 | A | 7.32 | 75.0 | 14.1 | 586 | 63.4 | 84.5 |
| 5 | A | 7.55 | 79.6 | 14.7 | 592 | 65.8 | 82.7 |

[1]0.5 wt. % Ge via impregnation with tetratphenyl germanium
[2]21,200 vanadium equivalents
[3]21.4° A.P.I.
[4]Gasoline is that portion of feed converted to C$_5$ and higher hydrocarbons boiling at a termperature up to 410° F. (210° C.) at atmospheric pressure.

As shown in Table V, catalyst A, which contained 0.5 part by weight germanium per 100 parts by weight cracking catalyst used in its preparation, was more active, produced less coke and less hydrogen, and provided more gasoline than catalyst O, to which no germanium had been added. Table V also shows that the selectivity to gasoline was approximately 15 percent higher with catalyst A than with catalyst O.

EXAMPLE II

To a slurry containing 25.24 g (0.10 mole) of potassium di-n-propyl-phosphorodithioate in benzene a solution of 5.36 g (0.025 mole) of germanium tetrachloride in benzene was added dropwise, at ambient temperature, with stirring. Stirring continued for an hour, then the mixture was heated to reflux temperature and held there for about 2 hours. After cooling, insoluble potassium chloride formed by the double decomposition reaction was removed from the solvent containing product by filtration through a bed of diatomaceous earth filter aid. Solvent was then removed from the product on a rotary evaporator.

The product, germanium tetrakis(di-n-propylphosphorodithioate) was calculated to be of the composition $C_{24}H_{56}O_8P_4S_8Ge$. The results of elemental analysis of the product and comparison with the calculated formula, are given in Table VI.

TABLE VI

| Element | Calculated | Found |
|---|---|---|
| C | 31.14 wt. % | 32.19 wt. % |
| H | 6.10 | 6.44 |
| P | 13.38 | 13.2 |
| S | 27.71 | 25.9 |
| Ge | 7.84 | 7.5 |

Samples of the passivating agent characterized by Table VI were employed to treat samples of catalyst O to impart to the samples germanium concentrations of 0.01, 0.05, 0.10 and 0.20 weight percent. This was accomplished by mixing with 40 g samples of catalyst O solutions of 40 mL of cyclohexane containing 0.051 g, 0.255 g, 0.51 g and 1.02 g of the above characterized germanium tetrakis(di-n-propylphosphorodithioate) and removal of the solvent by heating the mixture on a hot plate. The catalyst samples were then aged as in Example I and employed to catalytically crack a gas oil feedstock characterized as follows:

TABLE VII

| | |
|---|---|
| API gravity at 60° F. | 25.8 |
| Carbon residue, Ramsbottom | 0.87 |
| Elemental analysis | |
| Sulfur | 0.40 |
| Nitrogen | 0.07 |

The cracking and regeneration runs were conducted under the conditions set forth in Example I. Results of some runs with these catalysts are shown in Table VIII.

TABLE VIII

| Run No | Additive[1] | Cat[2]/Oil[3] Ratio | Conversion (Vol. % feed) | Yields Gasoline (Vol.%) | Yields Coke (wt.%) | Yields H$_2$(SCF/bbl conv) | Selectivity to Gasoline (%Conv) |
|---|---|---|---|---|---|---|---|
| 1 | None | 7.70 | 64.4 | 53.79 | 7.95 | 631 | 83.6 |
| 2 | 0.01 wt % Ge | 7.70 | 66.0 | 55.08 | 7.20 | 509 | 83.6 |
| 3 | 0.05 wt % Ge | 7.69 | 66.3 | 57.83 | 6.90 | 435 | 86.3 |
| 4 | 0.10 wt % Ge | 7.70 | 65.7 | 58.1 | 6.50 | 385 | 88.6 |

TABLE VIII-continued

| Run No | Additive[1] | Cat[2]/Oil[3] Ratio | Conversion (Vol. % feed) | Yields Gasoline (Vol.%) | Coke (wt.%) | H$_2$(SCF/bbl conv) | Selectivity to Gasoline (%Conv) |
|---|---|---|---|---|---|---|---|
| 5 | 0.20 wt % Ge | 7.68 | 64.6 | 56.74 | 6.40 | 408 | 87.8 |

[1]germanium tetrakis (di-n-propylphosphorodithioate)
[2]21,200 vanadium equivalents
[3]25.8° A.P.I.

In addition to the runs in Table VIII, additional runs with these catalysts were made at other catalyst/oil ratios, to vary conversion. From these runs (never fewer than five per catalyst), curves of conversion vs. catalyst/oil ratio were calculated, and the data in Table IX were obtained from the smoothed curves at constant conversion.

The incorporation of germanium into the cracking catalyst at levels of from 0.01 to 0.20 percent by weight was effective to increase its activity for cracking and its selectivity for gasoline production, and to decrease the selectivity of the cracking catalyst for hydrogen production and coke production. For the cracking catalyst tested, which contained over 20,000 ppm vanadium equivalents of nickel and vanadium, maximal benefit was observed at germanium concentrations of between 0.05 and 0.20 percent by weight, a weight ratio of elemental germanium to contaminants on the catalyst between about 1:10 to about 1:40.

ing the undesirable cracking behavior of metals contaminated zeolite containing cracking catalysts. Interestingly, it appears that germanium and antimony cooperate advantageously when present on the cracking catalyst in a weight ratio of about 1:10 to increase gasoline production and decrease hydrogen production. It is thus believed that germanium is effective to promote the passivation effects of antimony when present on the cracking catalyst in a weight ratio of germanium to antimony between about 1:100 to about 1:1.

TABLE X

| Run No | Additive[1] | Cat[2]/Oil[3] Ratio | Conversion (Vol. % feed) | Yields Gasoline (Vol.%) | Coke (wt.%) | H$_2$(SCF/bbl conv) | Selectivity to Gasoline (% Conv) |
|---|---|---|---|---|---|---|---|
| 1 | None | 7.7 | 64.3 | 53.6 | 7.8 | 630 | 83.3 |
| 2 | 0 Ge + 0.1Sb | 7.7 | 64.8 | 55.0 | 6.0 | 410 | 84.9 |
| 3 | 0.01 Ge + 0.1Sb | 7.7 | 65.5 | 57.0 | 6.4 | 360 | 87.1 |
| 4 | 0.05 Ge + 0.05Sb | 7.7 | 64.5 | 54.8 | 6.7 | 375 | 85.0 |
| 5 | 0.1 Ge + 0.01Sb | 7.7 | 64.0 | 55.0 | 6.3 | 410 | 86.0 |
| 6 | 0.1 Ge + 0Sb | 7.7 | 65.0 | 57.1 | 6.5 | 380 | 89.5 |

[1]Ge as Ge ((C$_3$H$_7$O)$_2$PS$_2$)$_4$; Sb as Sb ((C$_3$H$_7$O)$_2$PS$_2$)$_3$
[2]21,200 vanadium equivalents
[3]25.8° A.P.I.

TABLE IX

| Run No | Additive[1] | Cat[2]/Oil[3] Ratio | Conversion (Vol. % feed) | Yields Gasoline (Vol %) | Coke (wt.%) | H$_2$(SCF/bbl conv) | Selectivity to Gasoline (% Conv.) |
|---|---|---|---|---|---|---|---|
| 1 | None | 7.7 | 64 | 53.79 | 7.95 | 631 | 86.0 |
| 2 | 0.01 wt.% Ge | 7.0 | 64 | 53.85 | 6.83 | 493 | 84.1 |
| 3 | 0.05 wt.% Ge | 6.9 | 64 | 56.5 | 6.4 | 423 | 88.5 |
| 4 | 0.10 wt.% Ge | 7.1 | 64 | 57.5 | 6.10 | 378 | 89.9 |
| 5 | 0.20 wt.% Ge | 7.85 | 64 | 55.0 | 6.61 | 419 | 86.0 |

[1]Germanium tetrakis (di-n-propylphosphorodithioate)
[2]21,200 vanadium equivalents
[3]25.8° A.P.I.

EXAMPLE III

Five different catalysts were prepared by treating 40 grams of the equilibrium cracking catalyst characterized in Example I with solutions of antimony and/or germanium salts of di-n-propylphosphorodithioic acid in 40 mL cyclohexane. The salt solutions were mixed with samples of the cracking catalyst and the solvent removed by evaporation. The treated cracking catalyst samples containing the desired levels of germanium and/or antimony were then aged as described in Example I and employed to crack the gas oil feedstock characterized in Example II under the conditions described in Example I at 510° C. Some results of these runs are set forth in Table X.

Examination of the data presented in Table X reveals that germanium is about as good as antimony in reduc-

What is claimed is:

1. In a catalytic cracking process wherein a zeolite-containing cracking catalyst is circulated in a cracking unit between a cracking zone and a regeneration zone in a cyclic fashion, said process comprising:

(a) introducing the cracking catalyst and a hydrocarbon feedstock into the cracking zone, said hydrocarbon feedstock containing contaminants selected from the group consisting of nickel, vanadium, and iron;

(b) contacting the cracking catalyst with the hydrocarbon feedstock in the cracking zone under cracking conditions wherein at least a portion of the contaminants in the feedstock become deposited on the cracking catalyst;

(c) withdrawing an effluent of cracking catalyst and cracked hydrocarbon feedstock from the cracking zone;

(d) separating the cracking catalyst from the effluent;

(e) introducing the cracking catalyst into a regeneration zone;

(f) regenerating the cracking catalyst under elevated temperatures and in the presence of free oxygen-containing gas wherein contaminants deposited on the catalyst from the feedstock prevent complete regeneration of the cracking catalyst; and (g) recycling the cracking catalyst to the cracking zone; the improvement comprising circulating a germanium-treated cracking catalyst in the cracking unit, said germanium-treated cracking catalyst having been contacted with a germanium-containing treating agent under conditions to deposit thereon a sufficient amount of germanium or a germanium compound to at least partially passivate the at least one contaminant deposited on the catalyst from the feedstock.

2. A process as in claim 1 wherein said cracking catalyst is contacted with said treating agent so as to impart to said cracking catalyst a concentration of germanium in said cracking catalyst of from about 0.0001 to about 4 percent by weight of the cracking catalyst after contact.

3. A process as in claim 1 wherein said cracking catalyst is contacted with said treating agent so as to impart to said cracking catalyst a concentration of germanium in said cracking catalyst of from about 0.001 to about 2 percent by weight of the cracking catalyst after contact.

4. A process as in claim 1 wherein said cracking catalyst is contacted with said treating agent so as to impart to said cracking catalyst a concentration of germanium in said cracking catalyst of from about 0.01 to about 0.5 percent by weight of the cracking catalyst after contact, and wherein said cracking catalyst is contaminated with at least one contaminant selected from the group consisting of nickel, vanadium and iron in an amount of at least 3,000 ppm vanadium equivalents.

5. A process as in claim 1 wherein said cracking catalyst is contaminated with at least one contaminant selected from the group consisting of nickel, vanadium and iron in an amount of at least 10,000 ppm vanadium equivalents.

6. A process as in claim 4 wherein the ratio of the elemental weight of germanium to vanadium equivalents on the cracking catalyst is from about 1:5000 to about 5:1.

7. A process as in claim 5 wherein the ratio of the elemental weight of germanium to vanadium equivalents on the cracking catalyst is from about 1:1000 to about 1:1.

8. A process as in claim 1 wherein said at least one treating agent is contacted with said catalyst by impregnation of said catalyst with a solution of said treating agent.

9. A process as in claim 2 wherein said cracking catalyst is contacted with at least one treating agent selected from the group consisting of germanium oxide, germanium sulfide, germanium nitride, germanium halide, germanium selenide, germanium telluride, and germanium hydride.

10. In a catalytic cracking process wherein a zeolite-containing cracking catalyst is circulated in a cracking unit between a cracking zone and a regeneration zone in a cyclic fashion, said process comprising:

(a) introducing the cracking catalyst and a hydrocarbon feedstock into the cracking zone, said hydrocarbon feedstock containing contaminants selected from the group consisting of nickel, vanadium, and iron;

(b) contacting the cracking catalyst with the hydrocarbon feedstock in the cracking zone under cracking conditions wherein at least a portion of the contaminants in the feedstock become deposited on the cracking catalyst;

(c) withdrawing an effluent of cracking catalyst and cracked hydrocarbon feedstock from the cracking zone;

(d) separating the cracking catalyst from the effluent;

(e) introducing the cracking catalyst into a regeneration zone;

(f) regenerating the cracking catalyst under elevated temperatures and in the presence of free oxygen-containing gas wherein contaminants deposited on the catalyst from the feedstock prevent complete regeneration of the cracking catalyst; and (g) recycling the cracking catalyst to the cracking zone, the improvement comprising circulating a germanium-treated cracking catalyst in the cracking unit, said germanium-treated cracking catalyst having been contacted with a germanium-containing treating agent under conditions so as to impart to the cracking catalyst a concentration of germanium of between about 0.01 and about 0.5 weight percent, wherein the ratio of the elemental weight of germanium to vanadium equivalents of contaminants on the cracking catalyst is from about 1:500 to about 1:5.

11. In a catalytic cracking process wherein a zeolite-containing cracking catalyst is circulated in a cracking unit between a cracking zone and a regeneration zone in a cyclic fashion, said process comprising:

(a) introducing the cracking catalyst and a hydrocarbon feedstock into the cracking zone, said hydrocarbon feedstock containing contaminants selected from the group consisting of nickel, vanadium, and iron;

(b) contacting the cracking catalyst with the hydrocarbon feedstock in the cracking zone under cracking conditions wherein at least a portion of the contaminants in the feedstock become deposited on the cracking catalyst;

(c) withdrawing an effluent of cracking catalyst and cracked hydrocarbon feedstock from the cracking zone;

(d) separating the cracking catalyst from the effluent;

(e) introducing the cracking catalyst into a regeneration zone;

(f) regenerating the cracking catalyst under elevated temperatures and in the presence of free oxygen-containing gas wherein contaminants deposited on the catalyst from the feedstock prevent complete regeneration of the cracking catalyst; and (g) recycling the cracking catalyst to the cracking zone, the improvement comprising circulating a germanium-treated cracking catalyst in the cracking unit, said germanium-treated cracking catalyst having been contacted with a germanium-containing treating agent under conditions so as to impart to the cracking catalyst a concentration of germanium of between about 0.01 and about 0.5 weight percent, wherein said treating agent is incorporated into said hydrocarbon feedstock and contacted with said cracking catalyst in the cracking zone, to deposit on the cracking catalyst a sufficient amount of germanium to at least partially passivate the at least one contaminant deposited on the catalyst from the feedstock.

12. A process as in claim 11 wherein said hydrocarbon feedstock contains from 1 to about 800 parts per million of total effective metals.

13. A process as in claim 12 wherein said at least one treating agent is incorporated into said hydrocarbon feedstock in an amount in the range of from about 0.005 to about 500 parts per million by weight germanium to hydrocarbon feedstock.

14. A process as in claim 12 wherein said treating agent is incorporated into said hydrocarbon feedstock in an amount in the range of from about 1.5 to about 150 parts per million by weight germanium to hydrocarbon feedstock.

15. A process as in claim 11 wherein said cracking catalyst is contacted with at least one treating agent represented by the formula

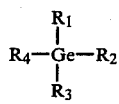

wherein $R_1$, $R_2$, $R_3$ and $R_4$ are independently selected from the group consisting of hydrogen, halogen, hydrocarbyl and oxyhydrocarbyl.

16. A process as in claim 15 wherein each R group has 1 to 20 carbon atoms and is selected from the group consisting of alkyl, cycloalkyl, and aryl.

17. A process as in claim 16 wherein said at least one treating agent comprises tetraphenylgermanium.

18. A process as in claim 11 wherein said cracking catalyst is contacted with at least one treating agent represented by the formula

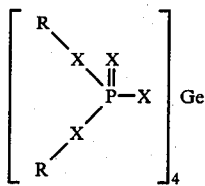

wherein R is hydrocarbyl having from 1 to 20 carbon atoms and X is selected from the group consisting of oxygen and sulfur.

19. A process as in claim 18 wherein said cracking catalyst is contacted with at least one treating agent represented by the formula

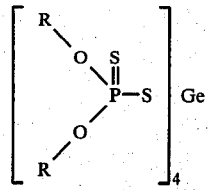

wherein R is hydrocarbyl having from 1 to 20 carbon atoms.

20. A process as in claim 19 wherein R is n-propyl.

21. In a catalytic cracking process wherein a zeolite-containing cracking catalyst is circulated in a cracking unit between a cracking zone and a regeneration zone in a cyclic fashion, said process comprising:
   (a) introducing the cracking catalyst and a hydrocarbon feedstock into the cracking zone, said hydrocarbon feedstock containing contaminants selected from the group consisting of nickel, vanadium, and iron;
   (b) contacting the cracking catalyst with the hydrocarbon feedstock in the cracking zone under cracking conditions wherein at least a portion of the contaminants in the feedstock become deposited on the cracking catalyst;
   (c) withdrawing an effluent of cracking catalyst and cracked hydrocarbon feedstock from the cracking zone;
   (d) separating the cracking catalyst from the effluent;
   (e) introducing the cracking catalyst into a regeneration zone;
   (f) regenerating the cracking catalyst under elevated temperatures and in the presence of free oxygen-containing gas wherein contaminants deposited on the catalyst from the feedstock prevent complete regeneration of the cracking catalyst; and
   (g) recycling the cracking catalyst to the cracking zone, the improvement comprising
   circulating a germanium-treated cracking catalyst through the cracking unit, said germanium-treated cracking catalyst having been contacted with a germanium-containing treating agent under conditions so as to impart to the cracking catalyst a concentration of germanium of between about 0.01 and about 0.5 weight percent, and with at least one antimony compound so as to impart to the cracking catalyst a weight ratio of germanium to antimony of between about 1:100 to about 1:1.

22. A process as in claim 21 wherein said treating agent comprises germanium di (n-propyl)-phosphorodithioate and said at least one additional treating agent comprises antimony tris (di-n-propylphosphorodithioate) in an amount sufficient to impart to said cracking catalyst a weight ratio of germanium to antimony of between about about 1:100 to about 1:1.

* * * * *

UNITED STATES PATENT AND TRADEMARK OFFICE
Certificate

Patent No. 4,334,979                                                      Patented June 15, 1982

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is Brent J. Bertus, Dwight L. McKay, H. Wayne Mark, and John S. Roberts.

Signed and Sealed this Twenty-seventh Day of May, 1986.

BRADLEY R. GARRIS,
*Office of the Deputy Assistant Commissioner for Patents.*